US00PP23205P2

(12) United States Plant Patent
Koppe

(10) Patent No.: US PP23,205 P2
(45) Date of Patent: Nov. 20, 2012

(54) ***BEGONIA* PLANT NAMED 'KRSSUWH01'**

(50) Latin Name: *Begonia×hiemalis*
Varietal Denomination: KRSSUWH01

(75) Inventor: Lubbertus H. Koppe, Putten (NL)

(73) Assignee: Koppe Royalty B.V., Putten (NL)

( * ) Notice: Subject to any disclaimer, the term of this patent is extended or adjusted under 35 U.S.C. 154(b) by 0 days.

(21) Appl. No.: 13/135,605

(22) Filed: Jul. 8, 2011

(51) Int. Cl.
*A01H 5/00* (2006.01)

(52) U.S. Cl. ..... Plt./345
(58) Field of Classification Search ..... Plt./345, Plt./344
See application file for complete search history.

*Primary Examiner* — Kent L Bell
(74) *Attorney, Agent, or Firm* — C. A. Whealy

(57) ABSTRACT

A new and distinct cultivar of *Begonia* plant named 'KRSSUWH01', characterized by its upright to outwardly spreading plant habit; freely branching habit; dark green-colored leaves; early and freely flowering habit; large semi double-type flowers that are white in color with yellow-colored centers; flowers are held above and beyond the foliar plane; and excellent postproduction longevity.

2 Drawing Sheets

Botanical designation: *Begonia×hiemalis.*
Cultivar denomination: 'KRSSUWH01'.

BACKGROUND OF THE INVENTION

The present invention relates to a new and distinct cultivar of *Begonia* plant, botanically known as *Begonia×hiemalis*, commercially known as Elatior *Begonia* and hereinafter referred to by the name 'KRSSUWH01'.

The new *Begonia* plant is a product of a planned breeding program conducted by the Inventor in Ermelo, The Netherlands. The objective of the breeding program is to create new vigorous *Begonia* plants with large semi double-type flowers and excellent postproduction longevity.

The new *Begonia* plant originated from a cross-pollination made by the Inventor in Ermelo, The Netherlands in January, 2007 of an unnamed proprietary selection of *Begonia×tuberhybrida*, not patented, as the female, or seed, parent with an unnamed proprietary selection of *Begonia socotrana*, not patented. The new *Begonia* plant was discovered and selected by the Inventor as a flowering plant from within the progeny of the stated cross-pollination in a controlled greenhouse environment in Ermelo, The Netherlands in September, 2007.

Asexual reproduction of the new *Begonia* plant by vegetative cuttings taken in a controlled greenhouse environment in Ermelo, The Netherlands since December, 2007 has shown that the unique features of this new *Begonia* plant are stable and reproduced true to type in successive generations.

SUMMARY OF THE INVENTION

Plants of the new *Begonia* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'KRSSUWH01'. These characteristics in combination distinguish 'KRSSUWH01' as a new and distinct *Begonia* plant:

1. Upright to outwardly spreading plant habit.
2. Freely branching habit.
3. Dark green-colored leaves.
4. Early and freely flowering habit.
5. Large semi double-type flowers that are white in color with yellow-colored centers.
6. Flowers are held above and beyond the foliar plane.
7. Excellent postproduction longevity.

Plants of the new *Begonia* differ primarily from plants of the female parent primarily in flower color as plants of the female parent selection have salmon-colored flowers.

Plants of the new *Begonia* differ primarily from plants of the male parent primarily in flower size and color as plants of the male parent selection have smaller pink-colored flowers.

Plants of the new *Begonia* can be compared to plants of *Begonia×hiemalis* 'White Netja', not patented. In side-by-side comparisons conducted in Ermelo, The Netherlands, plants of the new *Begonia* differed primarily from plants of 'White Netja' in the following characteristics:

1. Plants of the new *Begonia* had larger flowers than plants of 'White Netja'.
2. Plants of the new *Begonia* had semi double-type flowers whereas plants of 'White Netja' had double-type flowers.
3. Flowers of plants of the new *Begonia* had yellow-colored centers whereas flowers of plants of 'White Netja' had white-colored centers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'KRSSUWH01' grown in a container.

The photograph on the second sheet comprises close up views of the upper and lower surfaces of typical leaves (right); and open flowers of 'KRSSUWH01' (left, upper and lower views); and lateral surfaces of flower buds (left, center view).

DETAILED BOTANICAL DESCRIPTION

The aforementioned photographs and following observations and measurements describe plants grown during the spring in 13-cm containers in a glass-covered greenhouse in Ermelo, The Netherlands and under typical cultural practices. During the production of the plants, the average day temperature was 20° C. and the average night temperature was 18° C. Plants were twelve weeks old when the photographs and description were taken. In the following description, color references are made to The Royal Horticultural Society Colour Chart, 2007 Edition, except where general terms of ordinary dictionary significance are used.

Botanical classification: *Begonia×hiemalis* 'KRSSUWH01'.

Commercial classification: Elatior *Begonia.*

Parentage:

*Female, or seed, parent.*—Unnamed proprietary selection of *Begonia×tuberhybrida*, not patented.

*Male, or pollen, parent.*—Unnamed proprietary selection of *Begonia socotrana*, not patented.

Propagation:

*Type.*—By terminal vegetative cuttings.

*Time to initiate and develop roots, summer and winter.*—About 20 days at temperatures of 20° C.

*Time to produce a rooted young plant.*—About five weeks at temperatures of 20° C.

*Root description.*—Fine, fibrous; white to orange brown in color.

*Rooting habit.*—Freely branching; medium density; plants of the new *Begonia* have not been observed to form tubers.

Plant description:

*Plant habit.*—Upright and outwardly spreading plant habit, broad inverted triangle; freely branching with about eight lateral branches developing per plant; good stem and stem base strength; semi double-type flowers that are positioned above and beyond the foliar plane.

*Growth habit.*—Moderately vigorous growth habit; suitable for 12-cm and larger containers; under optimal environmental and cultural conditions, usually about twelve weeks are required to produce proportional plants in 13-cm containers; vegetative shoots are formed at basal nodes and main stem and flowering shoots are formed at upper nodes.

*Plant height.*—About 25 cm.

*Plant width.*—About 32.9 cm.

*Lateral branches.*—Length: About 9.8 cm. Diameter: About 8 mm. Internode length: About 2.8 cm. Angle: About 30° from vertical. Texture: Sparsely pubescent. Color: Close to 144A.

*Leaves.*—Arrangement: Alternate; simple. Length: About 11.1 cm. Width: About 10.1 cm. Shape: Deltoid to reniform. Apex: Acute. Base: Cordate; asymmetrical. Margin: Bi-serrate. Texture, upper surface: Smooth, glabrous; velvety. Texture, lower surface: Venation, sparsely pubescent. Venation pattern: Palmate. Color: Developing leaves, upper surface: Darker than 143A. Developing leaves, lower surface: Close to 148A. Fully expanded leaves, upper surface: Darker than between 139A and 147A; venation, close to 144A. Fully expanded leaves, lower surface: Close to 148A to 148B strongly tinged with close to 176A; venation, close to 144A. Petioles: Length: About 4.8 cm. Diameter: About 5 mm. Texture, upper and lower surfaces: Sparsely pubescent. Color, upper and lower surface: Close to 145A to 145B; distal spot, close to 185A. Stipules: Length: About 9 mm. Width: About 9 mm. Shape: Deltoid. Apex: Broadly acute. Base: Broadly cuneate. Margin: Entire. Texture, upper and lower surfaces: Smooth, glabrous. Color, upper and lower surfaces: Close to 174D; venation, close to 182A.

Flower description:

*Flowering habit.*—Semi double-type flowers with tepals arranged in axillary compound cymes; freely flowering habit with about 64 flowers developing per plant; numerous cymes in flower simultaneously; flowers face upright to outwardly and are positioned above and beyond the foliar plane.

*Natural flowering season.*—Early flowering habit, plants begin flowering about six weeks after pinching; plants flower under natural season conditions during the spring until the autumn in The Netherlands.

*Flower longevity.*—Individual flowers last about ten days on the plant; flowers not persistent; flowering plants have excellent postproduction longevity and typically maintain good substance for about six weeks under interior conditions.

*Inflorescence height.*—About 15.3 cm.

*Inflorescence diameter.*—About 9.6 cm.

*Flower buds.*—Length: About 2.3 cm. Diameter: About 0.9 cm to 2.4 cm. Shape: Orbicular, flattened. Color: Close to 145C to 145D.

*Flowers.*—Shape: Rounded; semi double-type. Diameter: Large, about 7.3 cm. Depth (height): About 2.2 cm.

*Tepals.*—Arrangement: Rosette. Quantity per flower: About 14 per flower in several whorls. Length: About 3.5 cm. Width: About 3.5 cm. Shape: Broadly obcordate to orbicular. Apex: Obtuse to lobed. Margin: Entire, moderately undulate. Texture, upper and lower surfaces: Smooth, glabrous; velvety. Color: When opening, upper and lower surfaces: Close to NN155C to NN155D; towards the base, close to 6C. Fully opened, upper and lower surfaces: Close to NN155C to NN155D; towards the base, close to 6C.

*Tepaloids.*—Arrangement: Rosette. Quantity per flower: About 28 per flower in multiple whorls. Length: About 1.8 cm. Width: About 1.5 cm. Shape: Obcordate. Apex: Obtuse to lobed. Margin: Entire to incised. Texture, upper and lower surfaces: Smooth, glabrous; velvety. Color, outer tepaloids: When opening, upper and lower surfaces: Close to NN155C to NN155D; towards the base, close to 6C. Fully opened, upper and lower surfaces: Close to NN155C to NN155D; towards the base, close to 6C. Color, inner tepaloids: When opening, upper and lower surfaces: Close to 8C to 8D; towards the base, close to 12A. Fully opened, upper and lower surfaces: Close to 8C to 8D; towards the base, close to 12A.

*Flower bracts.*—Quantity and arrangement: Two, opposite; sessile. Length: About 1.6 cm. Width: About 1.4 cm. Shape: Broadly ovate. Apex: Acute. Margin: Entire. Texture, upper and lower surfaces: Smooth, glabrous; velvety. Color, upper and lower surfaces: Close to 146B to 146D; venation, close to 182A.

*Peduncles*.—Length: About 8.9 cm. Diameter: About 4 mm. Angle: About 30° from vertical. Texture: Smooth, glabrous. Color: Close to 152B.

*Pedicels*.—Length: About 3.8 cm. Diameter: About 3 mm. Angle: About 10° from vertical. Texture: Smooth, glabrous. Color: Close to 164A to 164B.

*Reproductive organs*.—Stamens: Number per flower: About eight. Anther length: About 1 cm. Anther shape: Spatulate. Anther color: Close to 13A. Pollen: None observed. Pistils: Not observed.

*Seeds and fruits*.—Seed and fruit production have not been observed on plants of the new *Begonia*.

Disease/pest resistance: Resistance to pathogens and pests common to *Begonia* has not been observed.

Temperature tolerance: Plants of the new *Begonia* have been observed to tolerate high temperatures of about 35° C. and to be hardy to USDA Hardiness Zone 10.

It is claimed:

1. A new and distinct *Begonia* plant named 'KRSSUWH01' as illustrated and described.

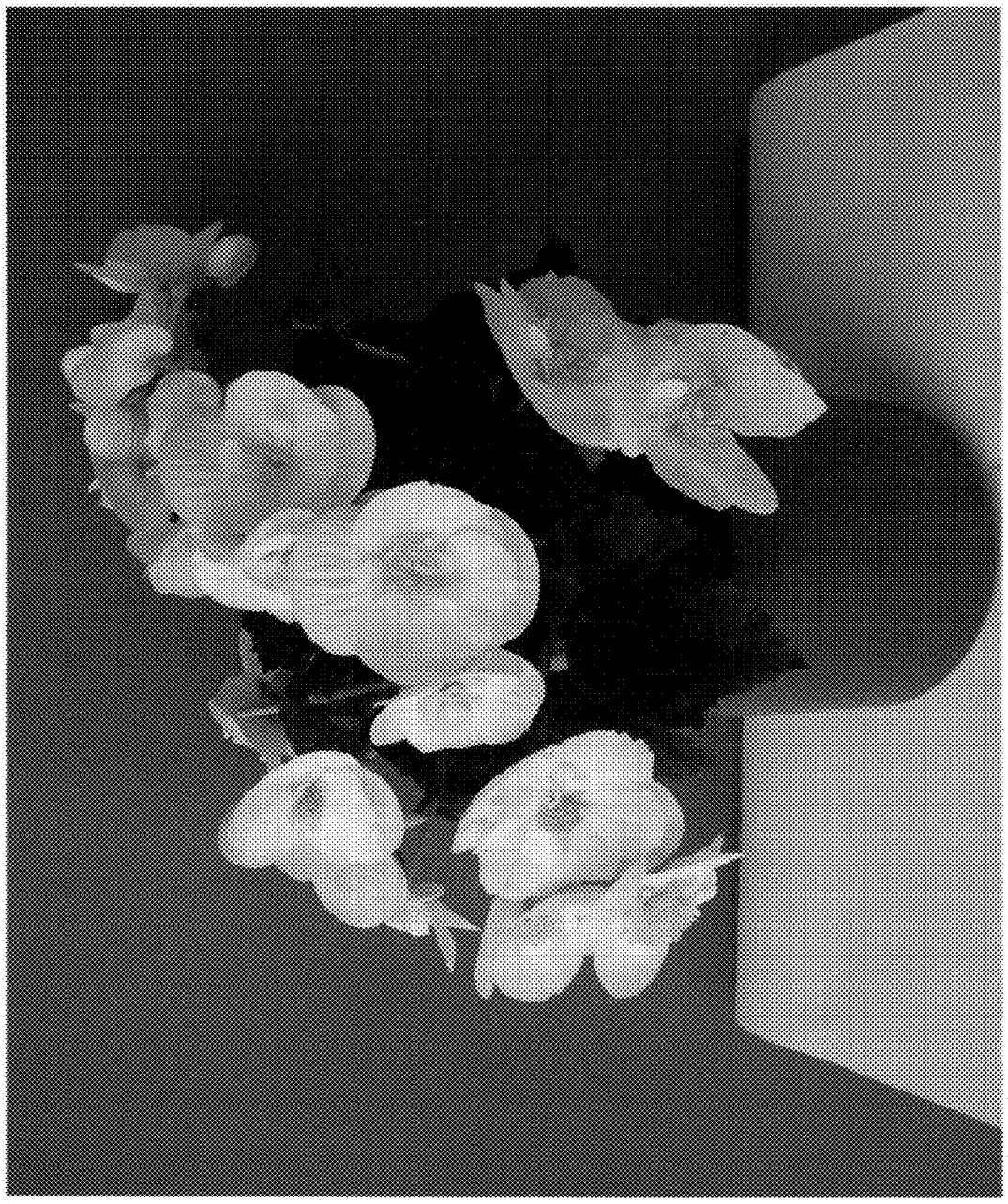

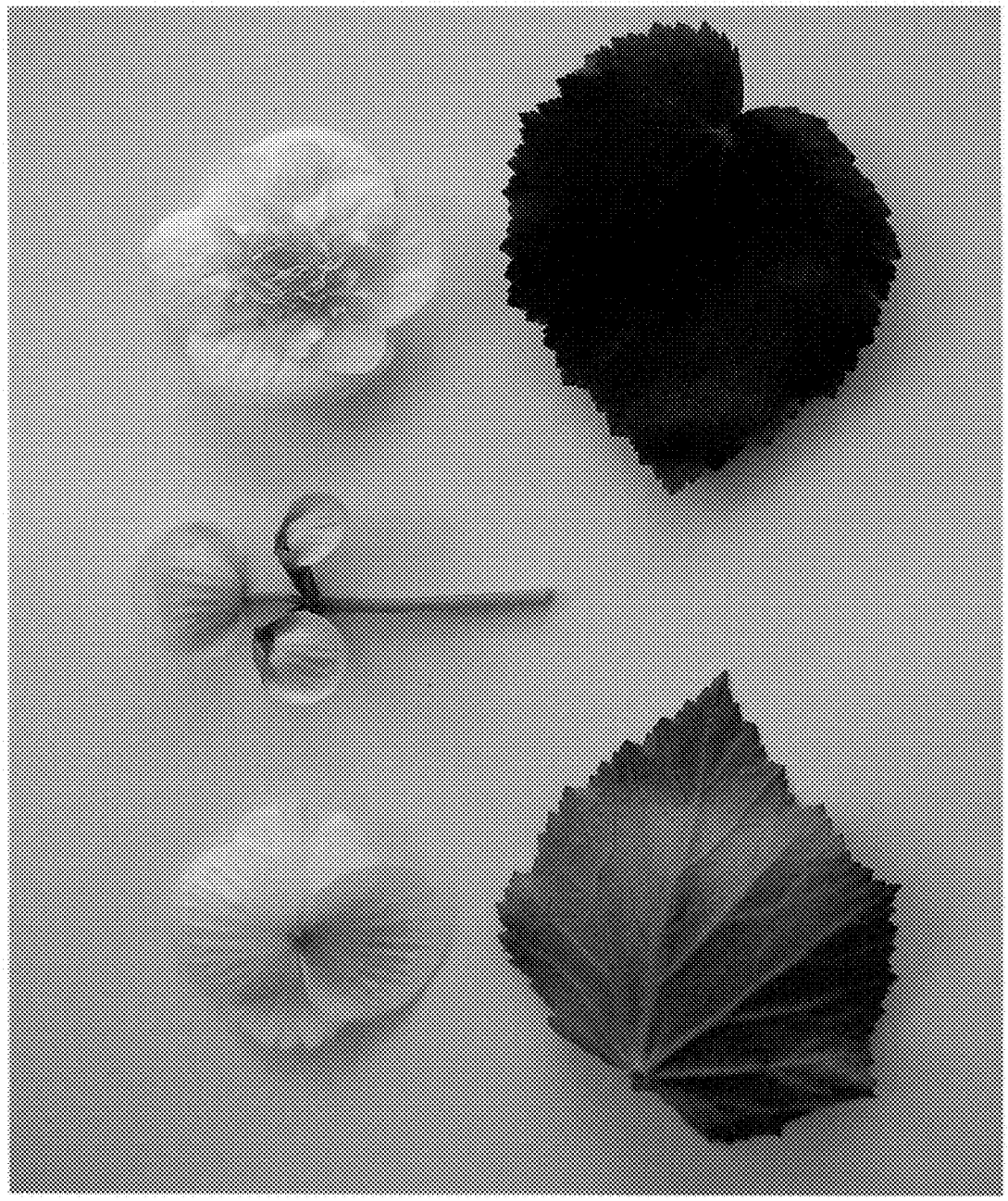

* * * * *